United States Patent [19]
Rodriguez et al.

[11] Patent Number: 5,616,501
[45] Date of Patent: Apr. 1, 1997

[54] RETICULOCYTE ANALYZING METHOD AND APPARATUS UTILIZING LIGHT SCATTER TECHNIQUES

[75] Inventors: Carlos M. Rodriguez, Miami; Stephen L. Ledis, Hialeah, both of Fla.

[73] Assignee: Coulter Corporation, Miami, Fla.

[21] Appl. No.: 560,423

[22] Filed: Nov. 17, 1995

Related U.S. Application Data

[62] Division of Ser. No. 306,346, Sep. 15, 1994, Pat. No. 5,492,833, which is a continuation of Ser. No. 62,857, May 14, 1993, abandoned.

[51] Int. Cl.$^6$ .................................................... G01N 33/48
[52] U.S. Cl. .......................... 436/63; 436/172; 436/175; 422/82.01; 422/82.02; 422/82.05; 422/82.08; 422/82.09; 356/39
[58] Field of Search ............................. 422/68.1, 81, 82, 422/82.01, 82.02, 82.05, 82.08, 82.09; 436/63, 172, 174, 175, 176; 356/39, 40

[56] References Cited

U.S. PATENT DOCUMENTS

| | | | |
|---|---|---|---|
| 4,325,706 | 4/1982 | Gershman et al. | 356/39 X |
| 4,336,029 | 6/1982 | Natale | 436/172 |
| 4,596,464 | 6/1986 | Hoffman et al. | 356/336 |
| 4,751,179 | 6/1988 | Ledis et al. | 435/34 |
| 4,791,355 | 12/1988 | Coulter et al. | 324/71.1 |
| 4,883,767 | 11/1989 | Lee et al. | 436/63 X |
| 4,985,174 | 1/1991 | Kuroda et al. | 252/408.1 |
| 4,989,978 | 2/1991 | Groner | 356/343 |
| 5,125,737 | 6/1992 | Rodriguez et al. | 356/39 |
| 5,194,909 | 3/1993 | Tycko | 356/40 |
| 5,284,771 | 2/1994 | Fan et al. | 436/10 |
| 5,350,695 | 9/1994 | Colella et al. | 436/63 |
| 5,492,833 | 2/1996 | Rodriguez et al. | 436/63 |

OTHER PUBLICATIONS

Bjorkman, S.E. "Method for Determining Absolute Reticulocyte Count," Clin. & Lab. Invest., 435–436, 10, 1958.

*Primary Examiner*—Jill Warden
*Assistant Examiner*—Maureen M. Wallenhorst
*Attorney, Agent, or Firm*—Mitchell E. Alter

[57] ABSTRACT

A reticulocyte analyzing method and apparatus in which a biological sample stream of ghosted red cells is passed into and through a point focused beam of light, such as laser light. A light detector structure is positioned with respect to the axis of the light beam to provide a light output pulse indicative of the passage of each cell. Electrically conductive contacts within the fluid stream can provide additional electrical pulse outputs of each cell. A staining reagent can be utilized with a ghosting reagent to further differentiate the reticulocytes. The light and the light and electronic produced output pulses or signals can be combined to define and quantify reticulocytes as distinct from other known cell types.

24 Claims, 14 Drawing Sheets

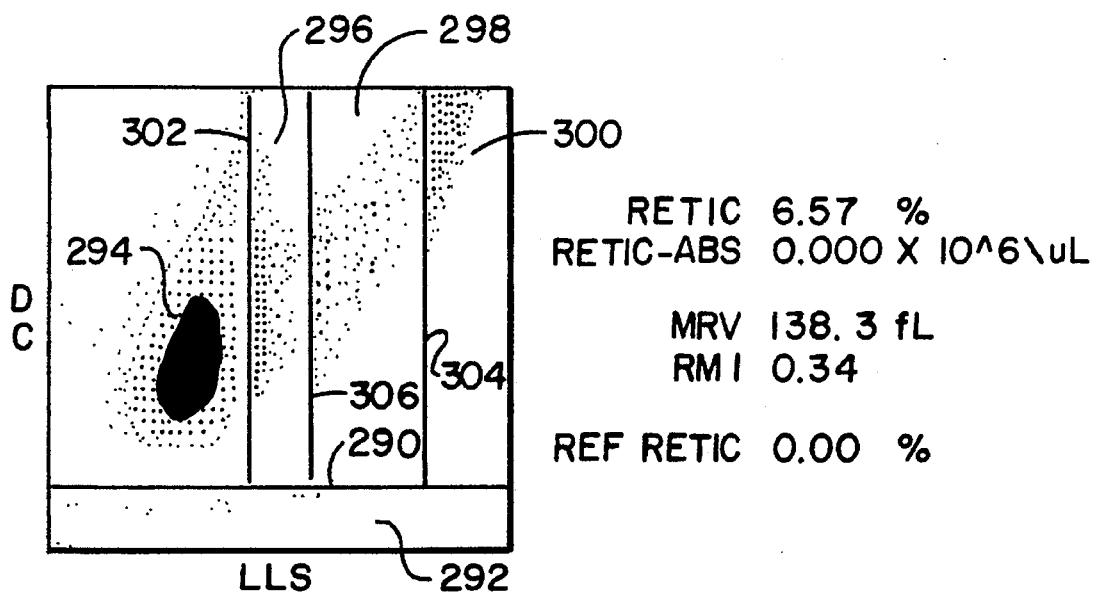
FIG. 6A
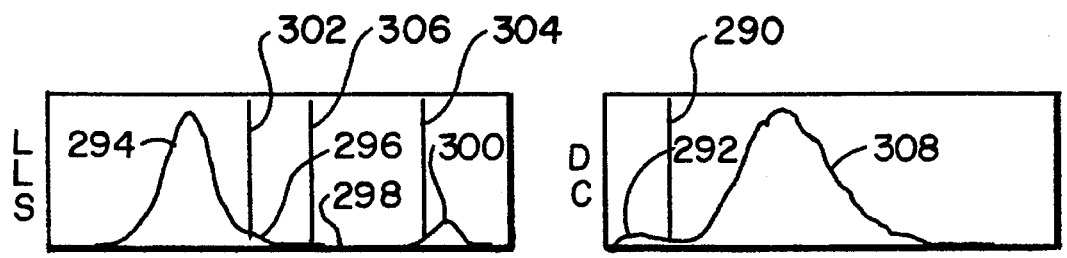
FIG. 6B  FIG. 6C

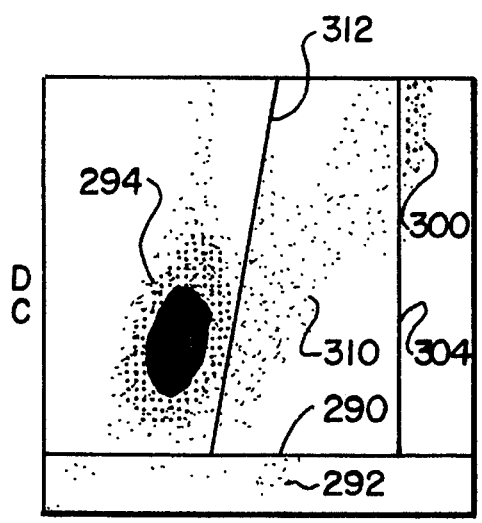
RETIC      5.76 %
RETIC-ABS        X 10^6\uL
MRV    140.5 fL
RMI    0.35
REF RETIC   0.00 %
FIG. 7A
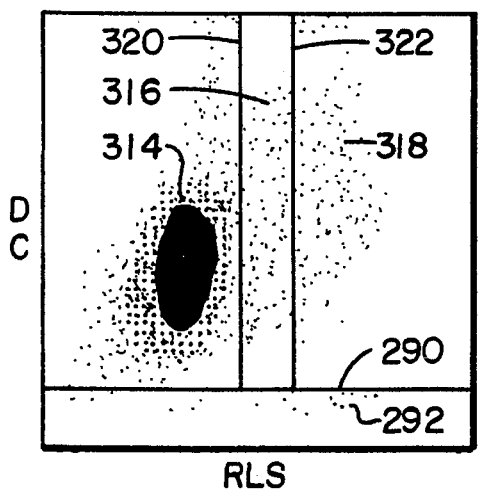
FIG. 7B
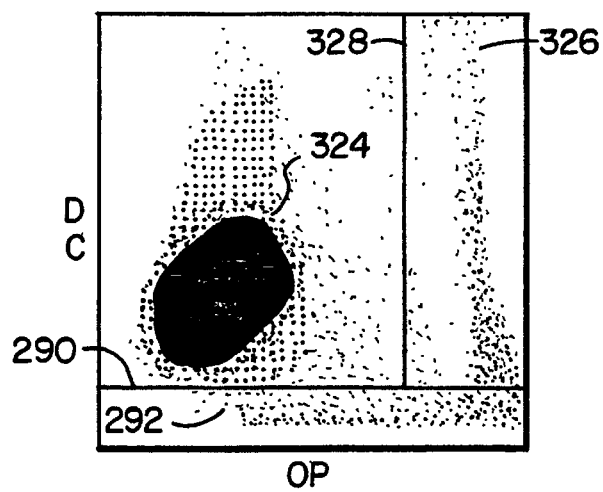
FIG. 7C
FIG. 7D
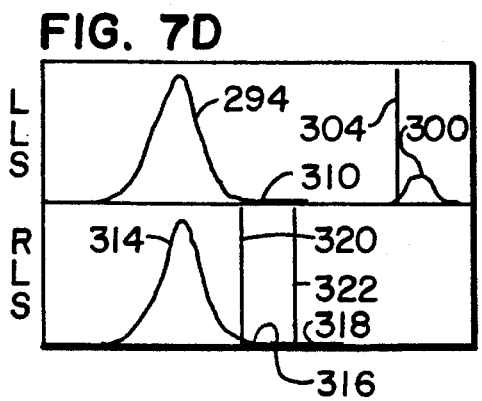
FIG. 7F
FIG. 7E
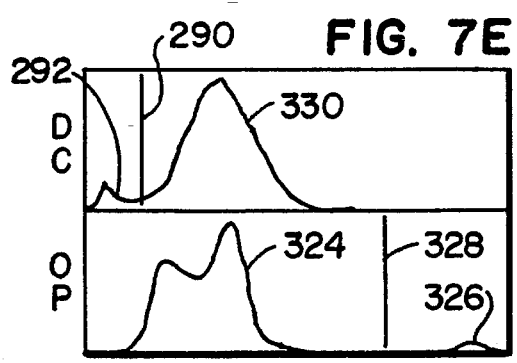
FIG. 7G

RETIC 0.24 %
RETIC-ABS 0.008 X 10^6\uL

MRV 105.3 fL
RMI 0.17

REF RETIC 0.00 %

RETIC 0.39 %
RETIC-ABS 0.014 X 10^6\uL

MRV 123.6 fL
RMI 0.28

REF RETIC 0.25 %

RETIC 0.68 %
RETIC-ABS 0.029 X 10^6\uL

MRV 119.3 fL
RMI 0.18

REF RETIC 0.55 %

```
      RETIC     1.46    %
 RETIC-ABS     0.044   X 10^6\uL

MRV    132.5    fL
       RMI     0.22

REF RETIC     1.70    %
```

```
      RETIC     1.73    %
 RETIC-ABS     0.067   X 10^6\uL

MRV    116.8    fL
       RMI     0.36

REF RETIC     1.52    %
```

```
      RETIC     2.30    %
 RETIC-ABS     0.087   X 10^6\uL

MRV    109.5    fL
       RMI     0.38

REF RETIC     2.63    %
```

| | | |
|---:|---:|:---|
| RETIC | 3.74 | % |
| RETIC-ABS | 0.120 | X10^6\uL |
| MRV | 139.6 | fL |
| RMI | 0.20 | |
| REF RETIC | 3.92 | % |

| | | |
|---:|---:|:---|
| RETIC | 5.31 | % |
| RETIC-ABS | 0.146 | X10^6\uL |
| MRV | 130.2 | fL |
| RMI | 0.44 | |
| REF RETIC | 6.35 | % |

| | | |
|---:|---:|:---|
| RETIC | 5.25 | % |
| RETIC-ABS | 0.126 | X10^6\uL |
| MRV | 161.4 | fL |
| RMI | 0.92 | |
| REF RETIC | 5.90 | % |

| RETIC | 10.30 | % |
| RETIC-ABS | | X10^6\uL |
| MRV | 122.0 | fL |
| RMI | 0.41 | |
| REF RETIC | 11.55 | % |

| RETIC | 25.00 | % |
| RETIC-ABS | 0.703 | X10^6\uL |
| MRV | 151.0 | fL |
| RMI | 0.88 | |
| REF RETIC | 28.00 | % |

| RETIC | 34.21 | % |
| RETIC-ABS | 0.657 | X10^6uL |
| MRV | 139.8 | fL |
| RMI | 0.75 | |
| REF RETIC | 30.10 | % |

RETICULOCYTE ANALYZING METHOD AND APPARATUS UTILIZING LIGHT SCATTER TECHNIQUES

This is a divisional of U.S. application Ser. No. 08/306,346, filed on Sep. 15, 1994 and now U.S. Pat. No. 5,492,833 issued on Feb. 20, 1996, which is a continuation of U.S. application Ser. No. 08/062,857, filed on May 14, 1993 and now abandoned.

BACKGROUND OF THE INVENTION

1. Field of the Invention

The present invention relates generally to a particle analyzing apparatus and more particularly to a method and apparatus for achieving selective, discriminate, differential classification of individual blood cell types, primarily reticulocytes utilizing light scatter-technology without the utilization of fluorescent staining techniques or materials.

2. Description of the Prior Art

Reticulocytes are defined in the medical literature as immature erythrocytes (or cells from which the nucleus has been extruded) and such cells normally account for 0.7 to 2.2 percent of the erythrocyte total count. In confirming or helping to confirm the diagnosis of diseases such as, for example, various forms of anemia or acute internal hemorrhage, the determination of reticulocytes can be of critical importance.

Microscopic examination of human blood smears on a glass slide is the universal accepted method of reticulocyte determination. This method is not only time consuming but relies on the human eye for the actual reticulocyte count. This often results in an inaccurate reticulocyte count which could also result in misdiagnosis.

One such microscopic method of determining reticulocytes is disclosed by Bjorkman, "Method for Determining Absolute Reticulocyte Count," *J. Clin. & Lab. Investigation*, 435–436, 1958. Therein, the described method utilizes new methylene blue to stain capillary blood and then fixes the blood cell with a diluent. The diluent fluid consists of potassium thiocyanate in dilute sulfuric acid. The fixation process is attended by an escape of hemoglobin from the blood cells. The decrease in hemoglobin content enhances the definition of the reticulum when the cell is viewed under a microscope in a blood smear on a slide.

Automated reticulocyte counting apparatus is available, but in the known instrumentation reliance is universal on the employment of fluorescence as a basis for the reticulocyte determination. Apparatus utilizing fluorescent devices are expensive, complex and require relatively costly maintenance.

It is well known that reticulocytes can be discriminated and classified by utilization of flow cytometry instrumentation when coupled with fluorescent staining. One such method involves utilizing low angle light scatter in combination with 90° or high angle light scatter.

The prior art literature, scientific papers and reports, illustrate, describe, and discuss the utilization of light scatter techniques at a variety of angular positions relative to the axis of the light beam being utilized to illuminate and interrogate the sample. However, the majority of the literature material available rely on the utilization of fluorescence and fluorescent techniques and chemistry to detect reticulocytes.

Examples of such prior art teaching includes U.S. Pat. No. 4,985,174 to Kuroda et al. which describes a reagent containing a dye which intensifies the strength of reticulocyte fluorescence in a stained sample and at the same time reduces the background fluorescence of the sample, so as to raise the signal to noise ratio when fluorescence is measured. This is accomplished by a reagent containing auramine O.

U.S. Pat, No. 4,325,706 to Gershman et al. relates to a method of treating a whole blood sample with acridine orange wherein the sample is passed through an optical flow cytometry cell having a narrowed hydrodynamic focal region. Red fluorescent light and forward scattered light are detected. Based on threshold comparisons, a threshold level is developed to separate the red cells from the reticulocytes.

U.S. Pat. No. 4,883,867 to Lee et al. relates to a fluorescent composition. The utilization of thiazole orange has been found to be an effective dye for staining reticulocytes.

SUMMARY OF THE INVENTION

The present invention provides a new, useful, and heretofore unobvious biological cell counting, measuring, and differentiating method and apparatus providing automatic high speed, accurate analysis and separation of cell types from each other within biological cell samples.

Broadly, the present invention provides a structural combination in which a biological sample of ghosted red cells, in the form of a hydrodynamically focused stream of particles, is passed into and through a point focused beam of light such as electromagnetic radiated energy, laser light. Light detector structure suitably positioned with respect to the axis of the light beam, provides a light output pulse indicative of the passage of each cell.

Electrically conductive contacts within the fluid stream pathway can provide additional electrical pulse outputs as the result of interrogation of each cell. Suitably placed photo receptors, angularly disposed with respect to the light beam axis, provide output electrical pulses indicative of the reticulocytes within the moving sample. By utilization of suitable electronic circuitry, the light and electronic produced output pulses or signals can be combined to define and quantify reticulocytes as distinct from other known cell types.

The present invention has to do with apparatus and method for generating data representative of reticulocytes by utilization of light scattering techniques alone and in combination with technology of the Coulter type.

Still more specifically, novel apparatus and methodology is provided by the present invention for utilizing the information or data derived from a light responsive pulse generating assembly which is arranged in the output area of a masked laser beam at a range of angles relative to the laser axis.

In the practice of the present invention, erythrocytes, treated with a lysing or "ghosting" reagent are analyzed by light scatter in a flow system, illuminated by a low-power laser, to provide detection and enumeration of reticulocytes, as a separate sub-population of erythrocytes.

The effect is evident in a wide range of light scattering angles, from low forward angles, e.g., 10°, up to and including approximately 180°. The preferred angle of analysis is from about 20° to about 65°.

Low frequency aperture impedance, also known as Coulter volume or DC, can be sensed simultaneously to identify and count all red cells, to discriminate erythrocytes from other cell types, and in addition, to obtain a mean reticulocyte volume.

High frequency or radio-frequency aperture impedance can be sensed simultaneously to further discriminate erythrocytes from other cell types.

BRIEF DESCRIPTION OF THE DRAWINGS

FIGS. 6A–C to 7A–G are data plots which illustrate reticulocyte analysis reports generated by automated population classification methods utilizing light or light and electronic sensing techniques;

DESCRIPTION OF THE PREFERRED EMBODIMENTS

Definitions

Figure 1:
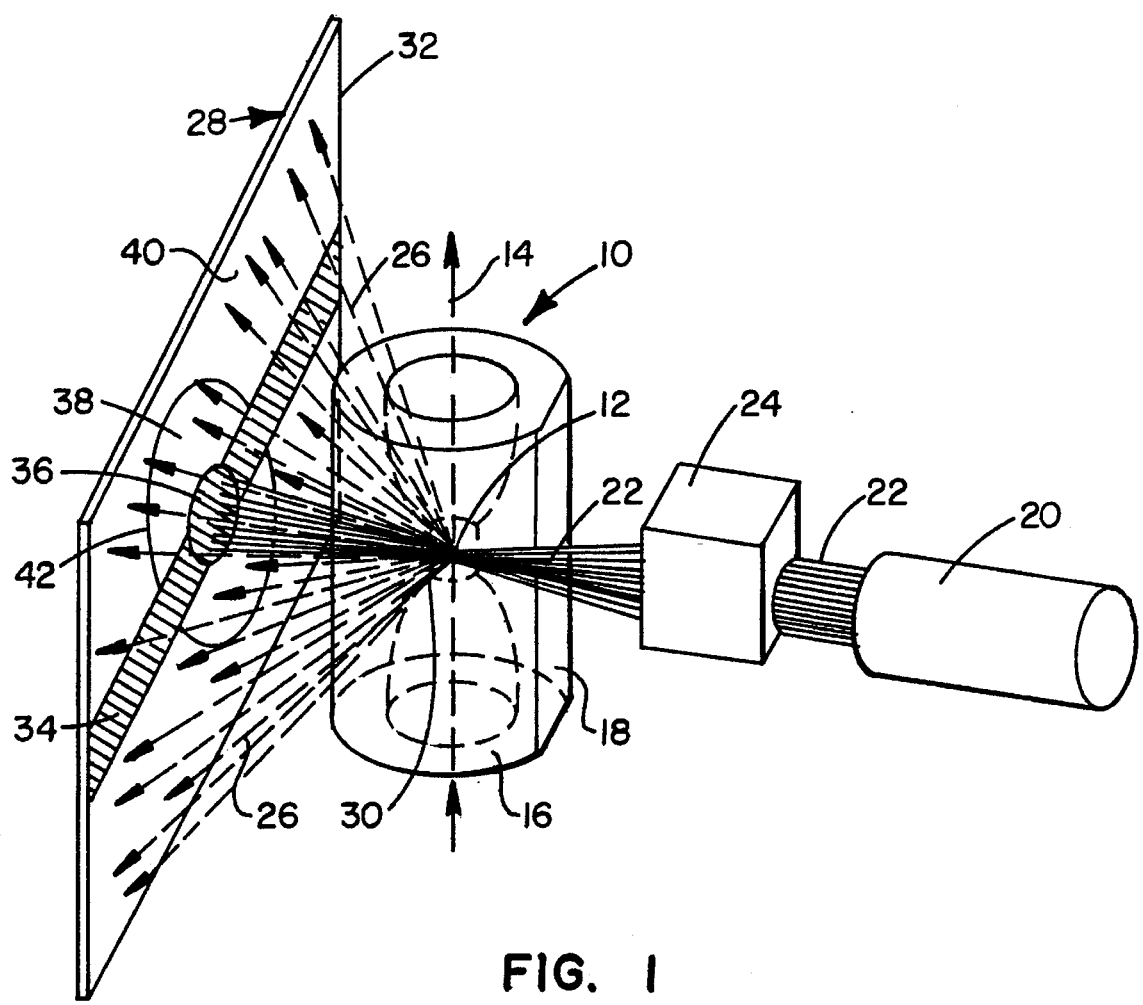
FIG. 1 is an idealized rendering of a cytometric flow cell and operably associated structure including a photodetector assembly.

In numerous figures and throughout the text of this specification, certain names and abbreviations will be utilized to obtain and/or describe the results obtained with the present invention.

"Histogram" is defined to be a graph of frequency distribution for a single variable, displayed as a two dimensional line graph with the variable plotted on the X axis and the frequency, designated as "#", plotted on the Y axis. Histogram also is defined as the abstract numerical tabulation of such a graph as represented within a computer or some other form of electrical circuit.

"Matrix" is defined to be a graph of frequency distribution for two independent variables, displayed as a three dimensional contour graph with one variable plotted on the X axis, the second variable plotted on the Y axis, and frequency or count displayed as iso-count contours. For clarity, only one iso-count contour will be displayed to illustrate population outlines. Matrix also is defined as the abstract numerical tabulation of such a graph as represented within a computer or some other form of electrical circuit. When describing a matrix in this Specification, the X axis variable will be listed first, followed by the Y axis variable.

"Parameter" is synonymous with independent variable and, in this invention as set forth in the following Specification, refers to any of the simultaneous, independent measurements obtained from particles or cells being analyzed in a flow cytometer. The combination of two or more parameters, by some mathematical function, is defined as yielding another parameter.

"Gating" is defined as a filtering process utilized in constructing, from multi-parameter data, a histogram of one parameter, while interrogating one or more of the other parameters. For each event, which is the passage of a single blood cell through the flow cell and the generation of cell measurements by the parameter transducers, the value or measurement corresponding to each parameter that is to be utilized for gating is compared with one or two reference values, or thresholds, and "tested" for being below the threshold, above the threshold, or between the two thresholds. If this test yields a true result for all the gating parameters being considered, then the event is included in the histogram. Gating also can be utilized to construct a matrix. Thus, by utilizing gating, it is possible to simplify the analysis and graphic representation of multi-parameter data.

"Photodetector" refers to any kind of device, vacuum or solid-state, which collects light and generates an electrical current proportional to the amount of light received by the photodetector.

"Beam dump" is defined as an obstruction for removing unwanted laser light, which generally appears as a horizontal line across the light detector as a result of the interaction between the laser beam and the flow cell, which if not blocked, degrades the detected light scatter signal.

"Mask" is defined as a circular or elliptical obstruction that removes unwanted low angle light scatter information, and prevents reception of this information by the light detector.

"DC" and "RF" are electronic sensing parameters which refer to the Coulter Principle of aperture impedance cell sensing. "DC" is defined as the pulse peak information obtained from applying a direct or low-frequency current, such that the cell membrane is not penetrated and no current flows through the cell. The peak amplitude of the DC pulse is a function of cell volume.

"RF" is defined as the pulse peak information derived from the measurement obtained from applying a high-frequency current, such that the cell membrane is short-circuited and current flows through the cell. RF is a function of cell volume and internal conductivity.

"Opacity" is defined as the signal value or data obtained by the division of the RF signal data by the DC signal data, for every individual cell measurement or event, yielding a new cellular parameter which is independent of size, but is a function of internal conductivity.

"LMALS" is defined as Lower Median Angle Light Scatter, which is light received at the photodetector assembly 28 scattered in or throughout the range of 10°–20° from the axis of the light beam, for example, the axis 30 of the laser beam 22.

"UMALS" is defined as Upper Median Angle Light Scatter, which is light received at the photodetector assembly 28 scattered in or throughout the range of 20°–65° from the axis of the light beam, for example, the axis 30 of the laser beam 22.

"RALS" is defined as Reverse Angle Light Scatter, which is light received at a photodetector assembly located in a reverse direction relative to the light beam 22 in the approximate angular range of 160°–176°.

"SALS" is defined as Side Angle Light Scatter, which is light received at a photodetector assembly located in an approximate angular range of 90°–20° from the axis of the light beam.

"RLS" is defined as Rotated Light Scatter, which is the log of UMALS divided by DC.

"RETIC" and "RETIC%" are both indicative of the reticulocyte count expressed as a percent of total erythrocytes.

"REF RETIC" is the reference reticulocyte percent obtained by following the microscopy-based methodology described in NCCLS document H-16P.

"RBC" is indicative of the absolute Red Blood Count, or erythrocyte count, which is usually expressed as count $\times 10^6/\mu L$.

"RETIC-ABS" is indicative of the absolute reticulocyte count usually expressed as count $\times 10^6/\mu L$.

"MRV" is defined as Mean Reticulocyte Volume, obtained by measuring the mean DC value for the reticulocyte population.

"RMI" and "MI" are both indicative of Reticulocyte Maturity Index which is defined as the ratio of the count of higher intensity light scatter reticulocytes to the total reticulocyte count.

"LS" is indicative of Light Scatter in general without specifying any particular angle or angular range.

"LLS" is defined as log of "LS". The preferred angle or angular range for LLS is LOG UMALS.

"RLS" is LLS, preferably LOG UMALS, divided by DC, as described earlier.

"LSR" is defined as Low intensity Scatter Reticulocytes.

"HSR" is defined as High intensity Scatter Reticulocytes. A more complete description of LSR and HSR is provided in a following section of this specification.

In the following description, light scatter angles are defined as the angles of the light exiting the biological cell within an aperture or sensing zone, still to be described. The angles of the scattered light striking a photodetector assembly, described hereinafter, can differ from the true angles within the aperture due to differences in indices of refraction of sample, diluent, and/or hydrodynamic sheath flow fluid, air, and the flow cell material, and also due to the architecture of the flow cell, as predicted by Snell's Law.

FIG. 1 illustrates a portion of a type of particle analyzing apparatus employing the method and process of the present invention. The apparatus of FIG. 1 includes a cytometric flow cell 10 which is made of any optically transparent material, for example fused silica. In this example, the interior of the flow cell 10 is cylindrical throughout its length, except for a narrowed or necked-down aperture 12 through which a biological cell sample is passed or flowed as a hydrodynamically focused stream 14 by well known means, not illustrated in this figure. An exterior wall surface 16 of the flow cell 10 is cylindrical, except for one side portion 18 which is flat.

A laser 20 emits a coherent light beam 22 into a lens or lens system 24 which focuses the beam 22 down to a small spot in the aperture or sensing zone 12. The laser 20 can be of any kind or wavelength.

Further, the invention is not limited to utilizing a laser as the light source. Other light sources, such as an arc lamp can be utilized, as long as the light can be focused down to a spot of the order of magnitude required for flow cytometric analysis. In this example, the laser 20 is a helium-neon laser of relatively low power, 0.8 mW, which emits at 632.8 nm. The lens system 24 includes two cross cylindrical lenses which are designed to focus the laser light beam 22 down to an elongated spot, aligned horizontally, within the aperture 12 of the flow cell 10. This optical shaping of the laser beam 22 makes the system less sensitive to cell or particle position, as the cells or particles flow through the flow cell 10, resulting in more uniform illumination and thus more uniform light scatter levels for identical cells or particles.

As the biological cells flow through the hydrodynamically focused stream 14, they pass individually through the aperture 12 and through the focused light beam 22, emitting light scatter rays 26 which are illustrated as dashed lines. A photodetector assembly 28, acting as a light scatter radiation receptor and positioned in a plane orthogonal to the axis 30 of the laser radiated light and centered on the axis 30, collects the light scatter rays 26.

Figure 1A:
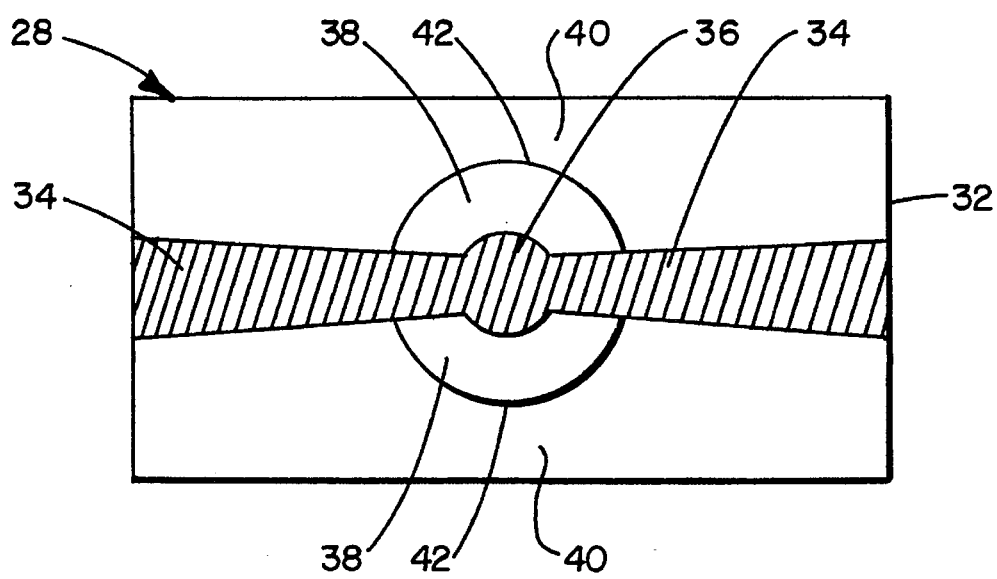
FIG. 1A is a front view (not to scale) of a photodetector assembly utilized with the present invention, illustrating the signal reception areas.

FIG. 1 illustrates the photodetector assembly 28 in an isometric view. FIG. 1A illustrates the same photodetector assembly 28 in a front plan view. The following discussion applies to both FIGS. 1 and 1A. The photodetector assembly 28 includes a photovoltaic detector 32 and a beam dump 34 and mask 36 combination which is placed in front of the detector 32 and horizontally aligned. The mask 36 is a circular or elliptical structure which is placed in the center of the beam dump 34. The mask 36 is oriented coaxial with the laser light beam axis 30.

The horizontal beam dump 34 can take the form of a bowtie, being larger or wider at the outer end thereof than at the center. The horizontal beam dump 34 is employed to accommodate the optics to the condition wherein the laser beam is shaped so as to be stretched or flattened in the horizontal direction to make the system less sensitive to cell or particle position, as the cells or particles flow through the flow cell 10. This optical shaping provides a more uniform light output signal for utilization in electronically utilizing the light scatter signal output.

In FIGS. 1 and 1A, the photodetector 32 is divided into two zones 38, 40 by a circular band 42. As a result of the dimensions of the photodetector 32, the dimensions of the zones 38 and 40, the dimensions of the mask 36, and as a result of the distance of the photodetector assembly 28 to the flow cell 10, the inner zone 38 receives LMALS light scattered in or throughout the range of approximately 10°–20°. The outer zone 40 receives LMALS light scattered in or throughout the range of 20°–65°.

For this description, blood cells are assumed to be passing, one by one, through the aperture 12 of the flow cell 10 illustrated in FIG. 1. A complete system description, which details how blood cells or other particles are introduced into the flow cell 10, and how multi-parameter data on the cells is obtained and processed in order to achieve classification, is provided in Assignee's U.S. Pat. No. 5,125,737.

Figure 2:
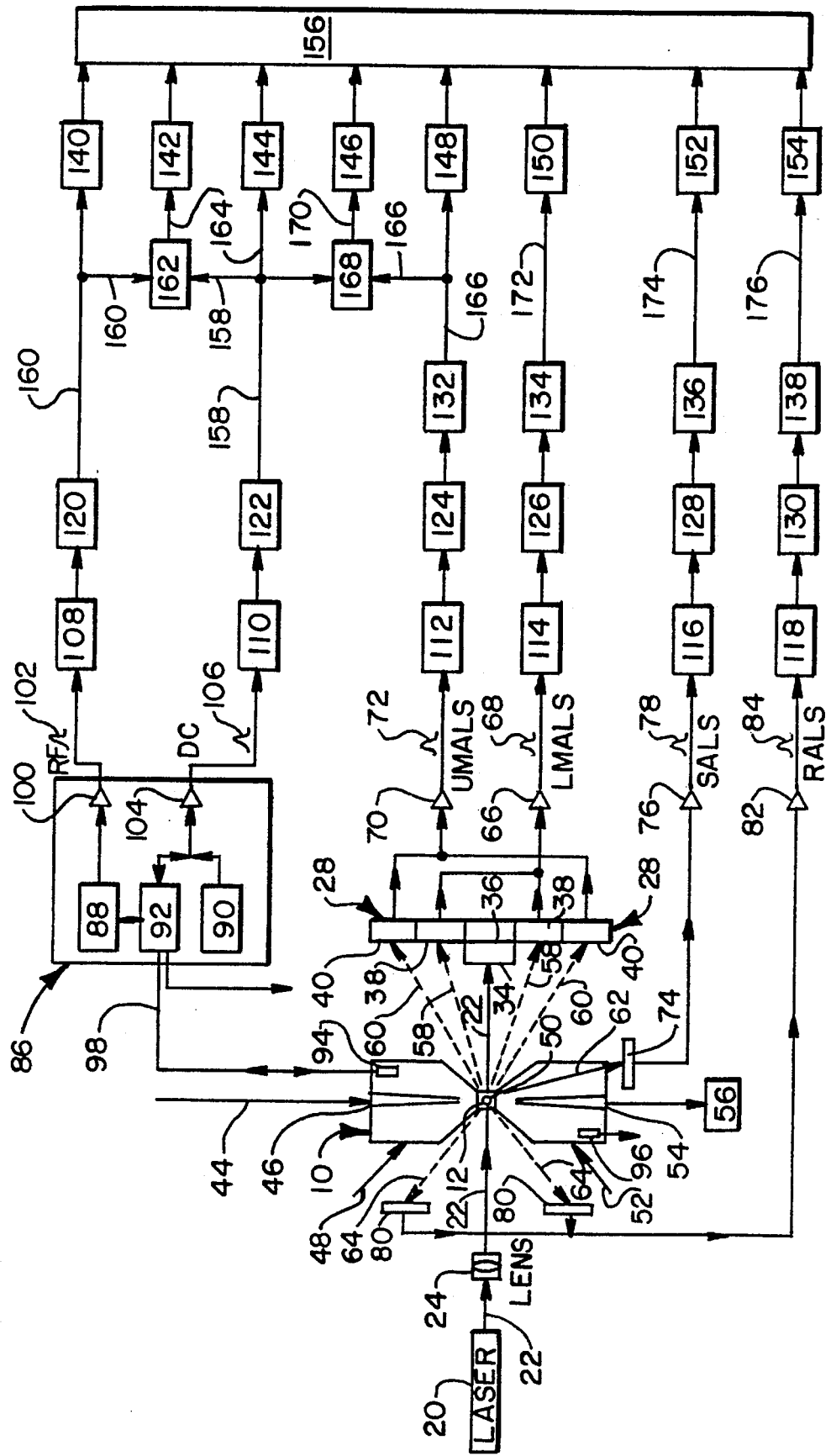
FIG. 2 is a system block diagram of an apparatus and operational electronic circuit for implementing the present invention.

FIG. 2 illustrates a block diagram of a particle analyzing apparatus, or flow cytometer, for implementing the present invention, which includes the components illustrated in FIG. 1 and FIG. 1A and previously described. The laser 20 emits a coherent beam 22 into a lens or lens system 24 which focuses the beam 22 down to a small spot in the aperture or sensing zone 12 of the cytometric flow cell 10. The beam 22 exits the flow cell 10 and strikes the mask 36 and beam dump 34 of the photodetector assembly 28. Blood cells in a dilution are introduced to the flow cell 10 through a line 44 and flowed through a sample introduction tube 46. A sheath fluid 48 hydrodynamically focuses the cells 50 to pass individually through the aperture 12. After the cells exit the aperture 12, a second sheath 52 directs them into a sample exit tube 54 and into a waste chamber 56. When a cell 50 is in the aperture 12 and is illuminated by the focused laser beam 22, it will scatter light in many directions. Certain light scatter rays 58, 60, 62 and 64 are illustrated as dashed lines.

The photodetector 32 of the photodetector assembly 28 includes the two zones 38, 40. The angular ranges of the two zones 38, 40 are determined by the dimensions of the photodetector 32, the distance and position of the photodetector 32 relative to the flow cell 10 and the diameter of the mask 36. The inner zone 38 collects the LMALS light rays 58 scattered in the approximate angular range of 10°–20°, producing a signal which is fed to a preamplifier 66 which outputs an LMALS pulse 68. The outer zone 40 collects the UMALS light rays 60 scattered in the approximate angular range of 20°–65°, producing a signal which is fed to a preamplifier 70 which outputs a UMALS pulse 72. A photodetector 74 is placed perpendicular to the axis 30 of the laser beam 22 (perpendicular to the plane of the figure) collecting the SALS light rays 62 scattered in the approximate angular range of 90°–20°, producing a signal which is fed to a preamplifier 76 which outputs a SALS pulse 78. A pair of photodetectors 80 are placed symmetrically about the laser beam 22 collecting the RALS light rays 64 scattered in a reverse direction relative to the laser beam 22, and in the approximate angular range of 160°–176°, producing a signal which is fed to a preamplifier 82 which outputs a RALS pulse 84.

An electrical source unit 86 provides electrical current source, detection, and amplification means for the RF and DC signals. Radio-frequency current from an oscillator-detector 88 and direct current from a DC source 90 are combined in a coupling circuit 92 and fed to a pair of electrodes 94, 96. The electrodes 94, 96 are located in the flow cell 10 on opposite sides of the aperture 12 in a known manner. The currents are combined via a line 98 establishing current flow through the aperture 12. The particle or cell 50 traversing the aperture 12 momentarily changes the impedance of the aperture 12, modulating the RF and DC components of the current through the aperture. The RF current modulation caused by this impedance change is filtered and fed through the coupling circuit 92, to the oscillator-detector 88, which provides a detected pulse to a RF preamplifier 100, which outputs an RF pulse 102.

Concurrently, the modulation to the direct current caused by the impedance change is filtered and fed through the coupling circuit 92, to a DC preamplifier 104, and which outputs a DC pulse 106. The above description of the electrical source unit 86 is a preferred form which is described fully in Assignee's U.S. Pat. No. 4,791,355 entitled "Particle Analyzer for Measuring the Resistance and Reactance of a Particle." The electrical source unit 86 can include any other design that is capable of yielding substantially the same results. Some embodiments of this invention utilize only DC and not RF currents; thus, in those cases, the electrical source unit 86 need contain only the DC source 90 and the DC preamplifier 104.

"Pulse processor" modules 108, 110, 112, 114, 116 and 118 each contain amplifier, low-pass and high-pass filters, and baseline restorers. "Peak detector" modules 120, 122, 124, 126, 128 and 130 each provide a "value" which is a steady voltage proportional to the pulse peak amplitude. Logarithmic amplifier modules (log amp) 132, 134, 136 and 138 are circuits that can be switched to provide as an output the logarithmic transform of the input or the unaltered, linear input. Analog-to-digital converters (ADC) 140, 142, 144, 146, 148, 150, 152 and 154 provide data to a computer 156 for further processing.

The DC pulse 106 is fed to pulse processor 110 and to peak detector 122 to produce a DC value on a line which is fed to ADC 144, which feeds the digitized pulse peak value to the computer 156. The RF pulse 102 is fed to pulse processor 108 and to peak detector 120 to produce an RF value on a line 160 which is fed to ADC 140, which feeds the digitized pulse peak value to the computer 156. A divider module 162 divides the RF value by the DC value and produces the opacity value on a line 164 which is fed to ADC 142, which feeds the digitized value to the computer 156.

The UMALS pulse 72 is fed to pulse processor 112, to peak detector 124 and through log amp 132 to produce a UMALS value on a line 166 which is fed to ADC 148, which feeds the digitized pulse peak value to the computer 156. A divider module 168 divides the log UMALS value by the DC value and produces the RLS value on a line 170 which is fed to ADC 146, which feeds the digitized value to the computer 156. The LMALS pulse 68 is fed to pulse processor 114, to peak detector 126 and through log amp 134 to produce an LMALS value on a line 172 which is fed to ADC 150, which feeds the digitized pulse peak value to the computer 156. The SALS pulse 78 is fed to pulse processor 116, to peak detector 128 and through log amp 136 to produce a SALS value on a line 174 which is fed to ADC 152, which feeds the digitized pulse peak value to the computer 156. The RALS pulse 84 is fed to pulse processor 118, to peak detector 130 and through log amp 138 to produce a RALS value on a line 176 which is fed to ADC 154, which feeds the digitized pulse peak value to the computer 156.

The reagent system utilized to enumerate the reticulocytes includes a red blood cell and reticulocyte ghosting solution comprising potassium thiocyanate and sulfuric acid. The function of the ghosting solution is to effectively swell the red blood cell to a spherical shape without bursting them and to permit hemoglobin to leak from the red blood cell. In addition, the ghosting solution has a fixative property so that the cell maintains the resulting spherical shape caused by the swelling.

The native reticulocyte has an irregular shape which produces unpredictable light scatter information in a flow cytometer when subjected to a light beam at angles from 0°–90°. The sphering of the red blood cell provides reproducible light scatter information which forms the basis for determining the reticulocytes in the sample.

The removal of hemoglobin from the swelled red blood cell is essential to this invention. The decrease in the hemoglobin content enhances the definition of the reticulum to permit flow cytometric determination of the reticulocytes.

It has been found that the ghosting process is effected by temperature. More specifically, it has been determined that temperatures below 55° F. appear to retard the ghosting process and longer time periods are necessary to permit the ghosting process to occur. As a result, it is preferred that the blood sample be mixed with the ghosting solution at a temperature of approximately 55° to approximately 106° F. for approximately 30 seconds. It has been determined that 106° F. (41° C.) provides the shortest time of ghosting.

The pH of the ghosting solution should be approximately 1.0 to 3.0, preferably 1.0 to 2.0. In addition, it appears that the acidic ghosting solution solubilizes the hemoglobin and facilitates its removal from the blood cell. It has been noted that when utilizing potassium thiocyanate, sulfuric acid is the preferred acid to be utilized in the combination. More specifically, other acids which did not work as well as sulfuric acid, include hydrochloric and nitric acids. The preferred concentration for the potassium thiocyanate is approximately from 1.0 to 6.0 grams per liter, and for the sulfuric acid is approximately from 0.7 to 3.0 grams per liter.

The osmotic pressure of the ghosting solution should be controlled so that there is a rapid, but controlled swelling of the blood cell. The osmotic pressure of the ghosting solution will range from 75 to 110 milliosmoles, and preferably 82 to 105 milliosmoles. The osmotic pressure causes the blood cell to swell and release the hemoglobin within thirty (30) seconds of mixing with the ghosting solution. If the osmotic pressure is less than 75 milliosmoles, then the blood cell will not retain an intact cell membrane and will lyse. More specifically, lower osmotic pressure results in red cells that are damaged so that reticulocyte enumeration is not reliable. If the osmotic pressure is not sufficient, the blood cells will retain hemoglobin which will obscure reticulocyte differentiation.

In a preferred embodiment of the present invention, a reticulocyte stain is employed before the ghosting procedure. The function of the reticulocyte stain is to further delineate the reticulocytes for light scatter enumeration in a flow cytometer. The reticulocyte stain is a non-fluorochrome dye that precipitates intracellular ribonucleic acid (RNA) of the reticulocyte. Examples of suitable stains include new methylene blue and brilliant cresyl blue. Utilizing a non-fluorescent dye to measure reticulocytes, allows the blood sample to be further analyzed for other constituents utilizing a fluorescent dye. More specifically, by utilizing a precipitating RNA dye for the enumeration of reticulocytes, a compatible fluorescent dye can be utilized in the same assay to investigate other components of the blood sample without interference from the fluorescence of the reticulocyte stain.

The preferred reticulocyte stain comprises an aqueous solution of new methylene blue. The aqueous new methylene blue solution has an alkaline pH and ranges from about 7.0 to 8.5 and preferably from 7.0 to 8.0. The aqueous new methylene blue solution has a stain concentration range from 0.2 to 2.0 grams per liter and preferably from 0.4 to 1.2 grams per liter. Moreover, the osmotic pressure of the stain solution ranges from approximately 120 to 160 milliosmoles, and preferably from 130 to 150 milliosmoles.

It has been found that the staining reaction time is shortened by higher temperatures, while at lower temperatures a longer reaction time is required. The preferred temperature range for the reaction is from 60° to 90° F. Utilizing this temperature range, the reaction time needed for the stain to sufficiently react with the blood cell is at least 5 minutes.

In the preferred method for analyzing a blood sample for reticulocytes, anticoagulated blood is employed. The anticoagulants used are EDTA salts, such as dipotassium, tripotassium and disodium salts.

It has been found that the staining of the cells is enhanced by increasing the alkalinity of the blood sample and stain mixture to range from pH 7.0 to 7.5. However, the staining is non specific and does not enhance the differentiation of the reticulocytes. Rather, the staining offsets the light scatter signal to a higher channel.

In addition, the reticulocyte stain should include antimicrobial agents as preservatives. Preferred antimicrobials are propylparaben, methylparaben and combinations thereof. More preferred antimicrobial agents are a combination of propylparaben at a concentration of 0.3 grams per liter and methylparaben at a concentration of 0.5 grams per liter.

The following specific examples of the staining and ghosting reagents are utilized in obtaining the results illustrated in FIGS. 4–12.

| Staining Reagent #1 | $K_3$EDTA | 10 g/L |
|---|---|---|
| | New methylene blue | 0.6 g/L |
| | NaCl | 2 g/L |

-continued

| Ghosting Reagent #1 | KSCN | 3 g/L |
|---|---|---|
| | 1N $H_2SO_4$ | 30 mL/L |

Figure 3A:
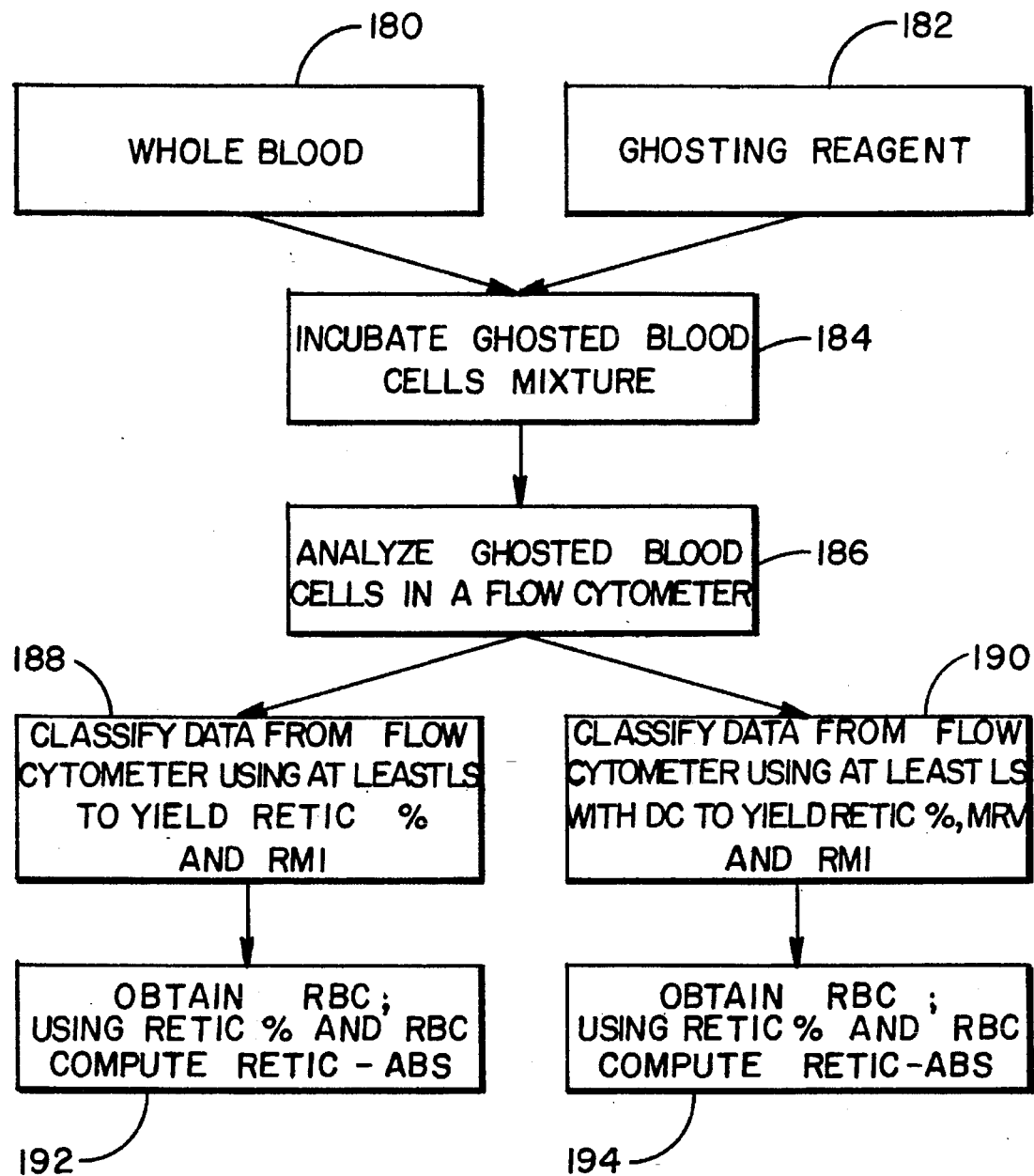
FIGS. 3A–C are flow diagrams illustrating three methods for differentiating and enumerating reticulocytes according to this invention.
Figure 3B:
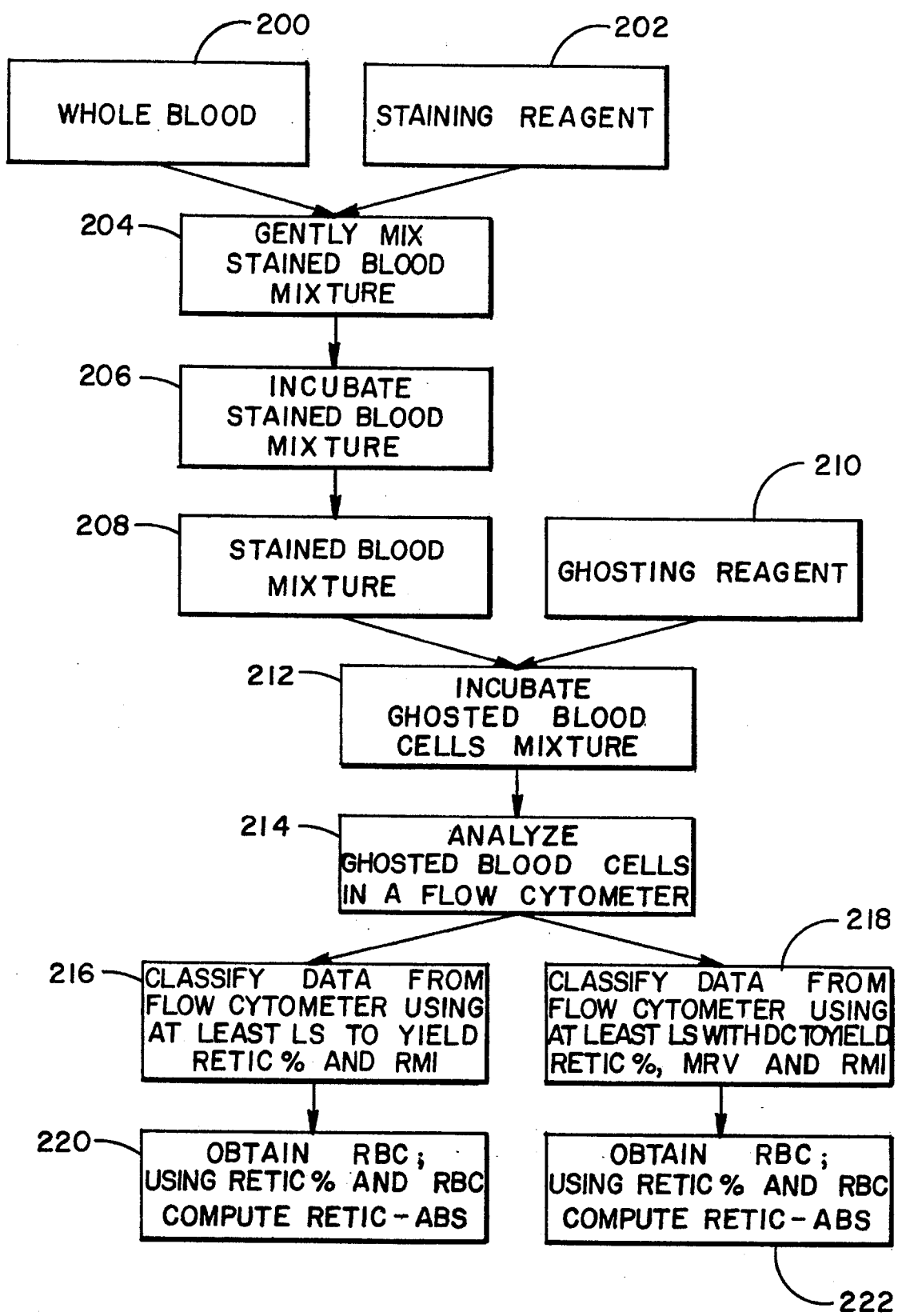
Figure 3C:
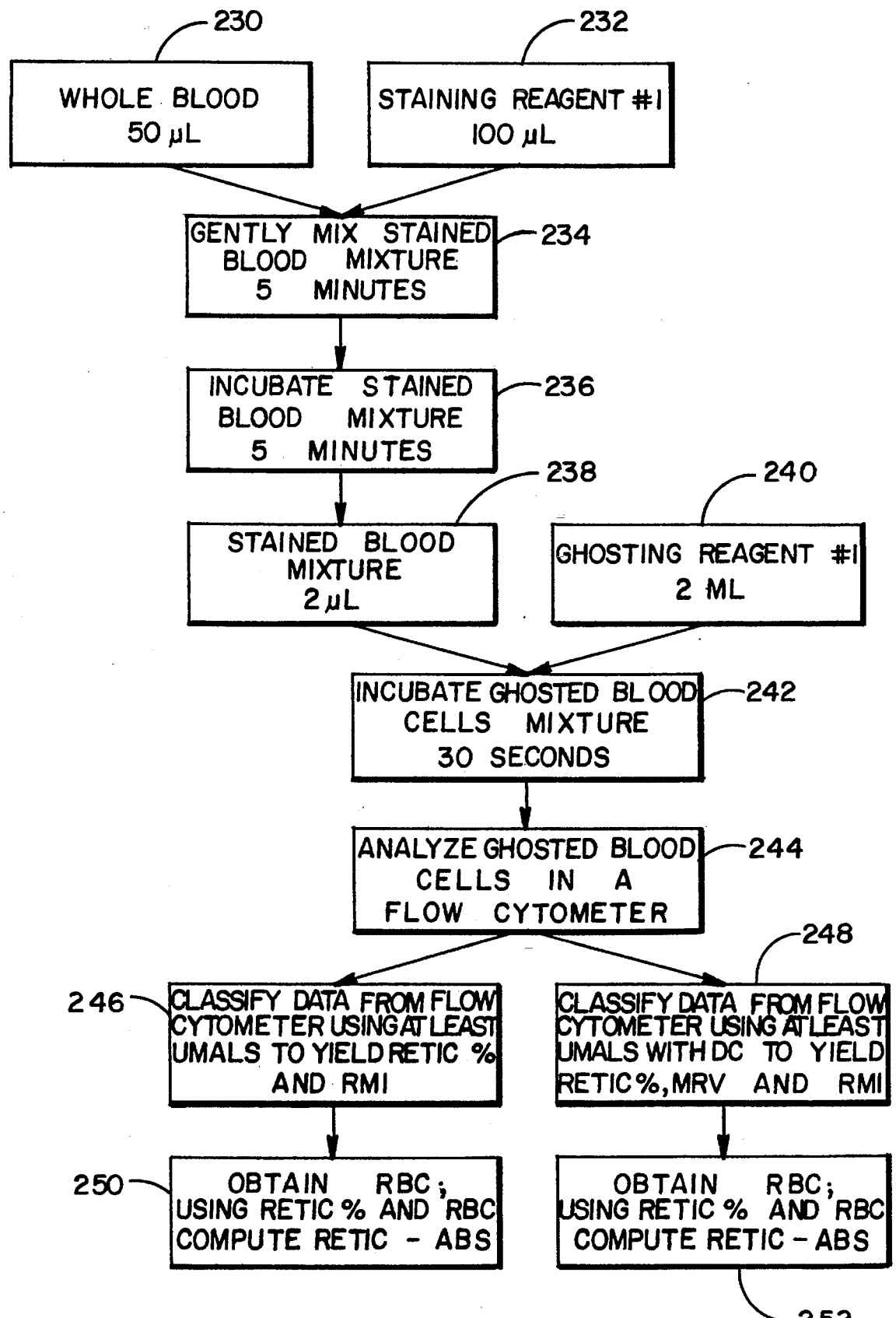

FIGS. 3A–C represent various operations of an apparatus or methods of preparing and analyzing blood samples to obtain reticulocyte classification and enumeration.

FIG. 3A illustrates two methods or operations of an apparatus for classifying and enumerating reticulocytes in step or flow diagram format. In both operations, a whole blood sample or portion 180 is treated with a ghosting reagent 182. The ghosted blood mixture is incubated 184 and analyzed in a flow cytometer 186. In the first option, the data from the flow cytometer is classified 188 using at least LS to yield RETIC% and RMI. In the second option, the data from the flow cytometer is classified 190 using at least LS with DC to yield RETIC%, MRV and RMI. With both options, RETIC-ABS then is obtained 192, 194 by multiplying RETIC% by RBC.

FIG. 3B illustrates two other methods or operations of an apparatus for classifying and enumerating reticulocytes. In both operations, a whole blood sample or portion 200 is treated with a staining reagent 202. The stained blood mixture is gently mixed 204 and incubated 206. The stained blood mixture 208 then is treated with a ghosting reagent 210. The ghosted blood mixture is incubated 212 and analyzed in a flow cytometer 214. Again as a first option, the data from the flow cytometer is classified 216 using at least LS to yield RETIC% and RMI. In the second option, the data from the flow cytometer is classified 218 using at least LS with DC to yield RETIC%, MRV and RMI. With both options, RETIC-ABS is obtained 220, 222 by multiplying RETIC% by RBC.

FIG. 3C illustrates yet two other methods or operations of an apparatus for classifying and enumerating reticulocytes. In both cases, 50 µL of whole blood 230 is treated with 100 µL of Staining Reagent #1 232. The stained blood mixture is gently mixed 234 for 5 seconds and incubated 236 for 5 minutes. A 2 µL portion of the stained blood mixture 238 then is treated with 2 mL of Ghosting Reagent #1 240. The ghosted blood mixture is incubated 242 for 30 seconds and analyzed in a flow cytometer 244. In a first option 246, the data from the flow cytometer is classified using at least UMALS to yield RETIC% and RMI. In the second option 248, the data from the flow cytometer is classified using at least UMALS with DC to yield RETIC%, MRV and RMI. With both options, RETIC-ABS is obtained by multiplying RETIC% by RBC 250, 252.

Figure 4A:
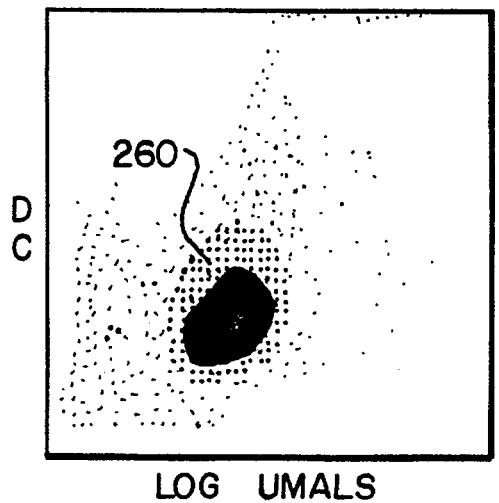
FIGS. 4A–D are data plots which illustrate the effect of staining and ghosting on a blood specimen containing reticulocytes.

FIGS. 4A–D illustrate the effect of staining and ghosting on reticulocytes, analyzed in a particle analyzer or flow cytometer such as illustrated in FIG. 2. Each of the four figures is a matrix, or two-dimensional dot plot, of LOG UMALS vs. DC (LOG UMALS on the x axis and DC on the y axis) of the same whole blood specimen prepared with different combinations of the staining and the ghosting reagents. Other light scatter angular measurements, such as LMALS, SALS and RALS can be utilized, but UMALS is preferred. FIG. 4A illustrates the data pattern obtained by diluting a whole blood sample in a balanced electrolyte solution commonly utilized as a diluent in hematology analyzers sold by the assignee of the present invention and without any other treatment including a staining reagent or a ghosting reagent. One such solution is sold under the name ISOTON® II, by the assignee of the present invention.

Figure 4B:
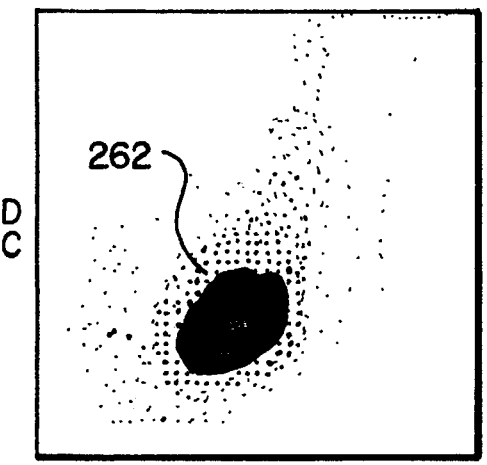
Figure 4C:
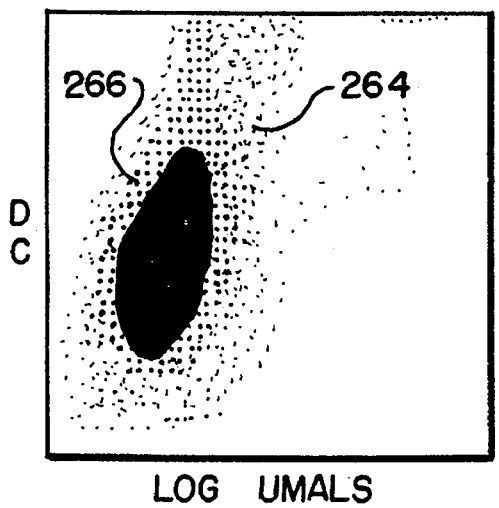
Figure 4D:
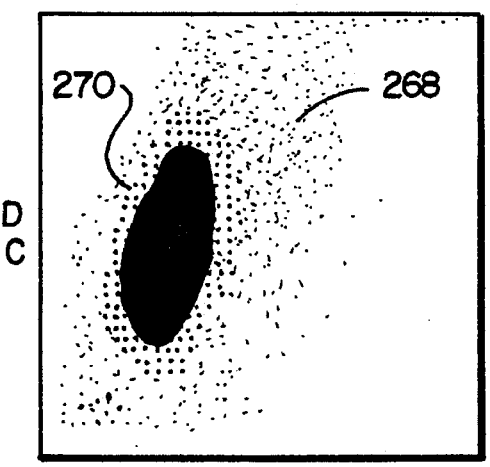

It is evident in FIG. 4A that there is a single population 260, identifiable by LOG UMALS, which consists of erythrocytes and reticulocytes data massed together. FIG. 4B displays the data pattern obtained by treating the whole blood sample with the staining reagent only and not utilizing the ghosting reagent. The pattern of FIG. 4B is very similar to that of FIG. 4A, illustrating a single population 262 of erythrocytes and reticulocytes together, as identified by LOG UMALS. FIG. 4C displays the data pattern obtained by treating the whole blood sample with the ghosting reagent only and not with the staining reagent, illustrating a population of reticulocytes 264 to the right or a higher level of LOG UMALS than the mature erythrocytes 266. FIG. 4D displays the data pattern obtained by treating the whole blood sample with both the staining reagent and the ghosting reagent, illustrating a population of reticulocytes 268 to the right or a higher level of LOG UMALS than the mature erythrocytes 270, and better separated than the reticulocyte population 264 of FIG. 4C.

From the data illustrated in FIGS. 4A–D and the description thereof, it can be concluded that the minimum requirement to identify and enumerate reticulocytes by utilizing light scatter without fluorescence is to treat the blood sample with a ghosting reagent. It can also be concluded that treating the blood sample with both a staining reagent and a ghosting reagent results in the optimum configuration for identifying and enumerating reticulocytes with light scatter and without utilizing fluorescence.

Figure 5A:
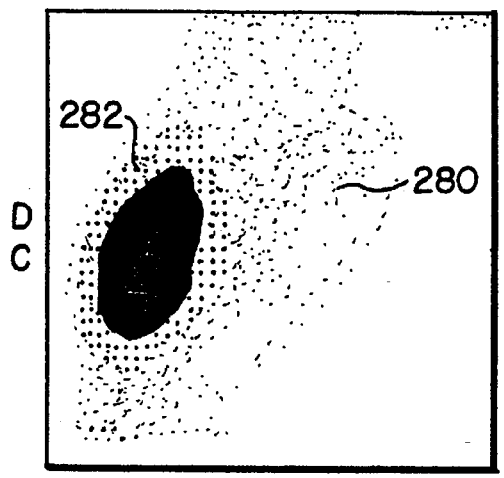
FIGS. 5A–D are data plots which illustrate the results obtained at various angles of light scattering of a blood specimen containing reticulocytes.
Figure 5B:
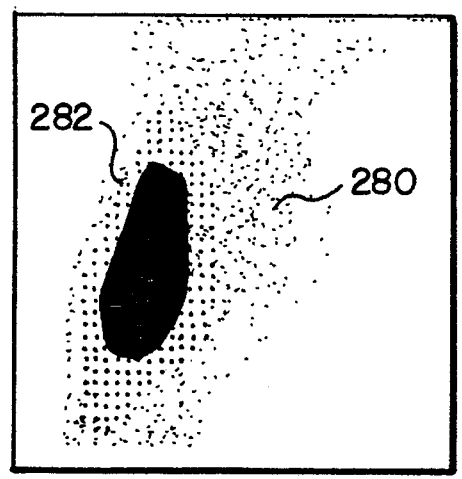
Figure 5C:
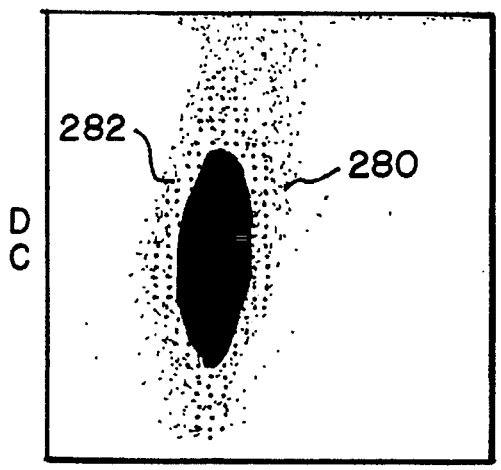
Figure 5D:
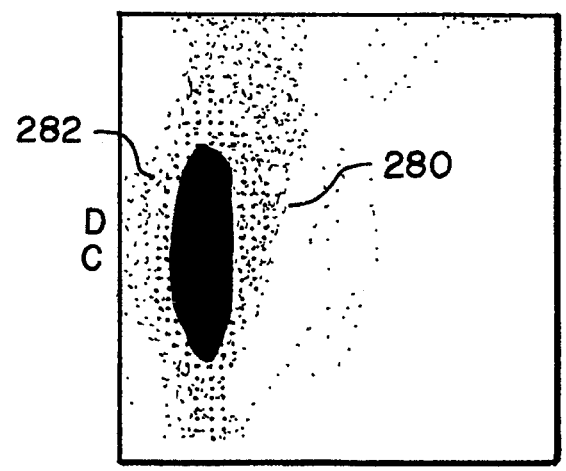
Figure 8A:
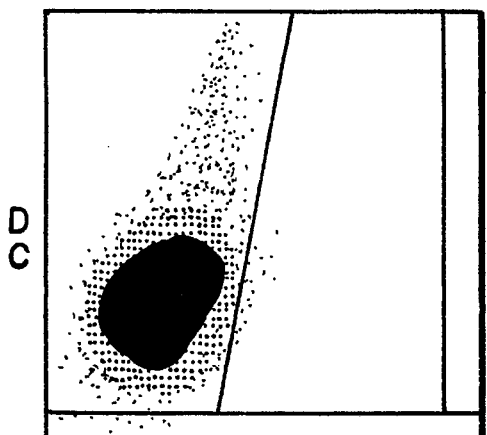
FIGS. 8A–C, 9A–C, 10A–C and 11A–C are data plots which illustrate reticulocyte analysis reports for numerous clinical human blood samples in a broad range of reticulocytes from 0.0 percent to about 30 percent.
Figure 8B:
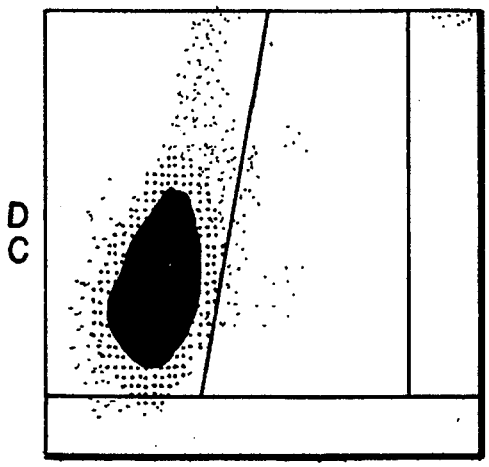
Figure 8C:
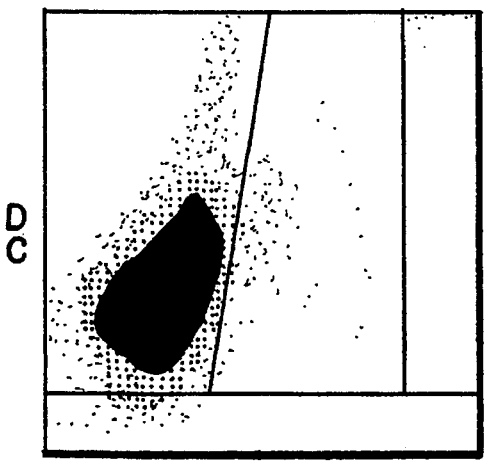
Figure 9A:
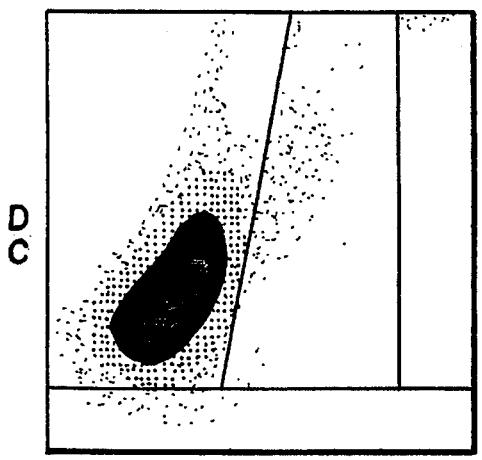
Figure 9B:
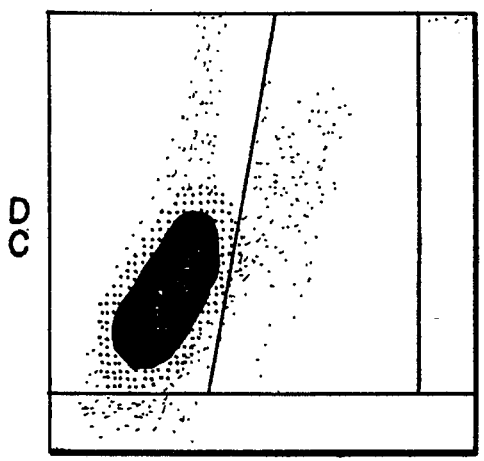
Figure 9C:
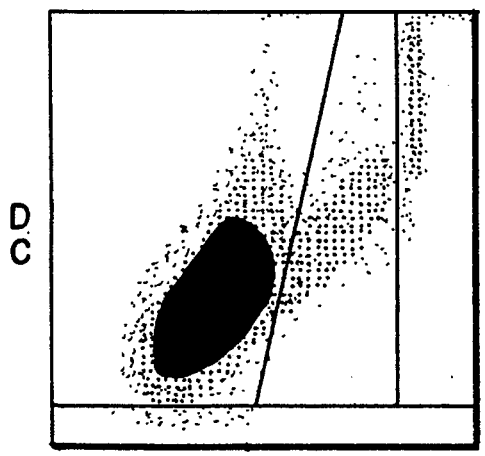
Figure 10A:
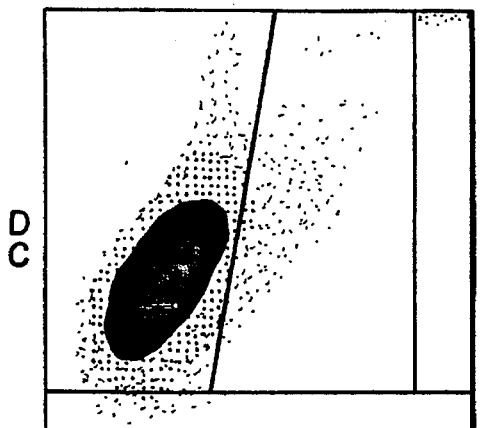
Figure 10B:
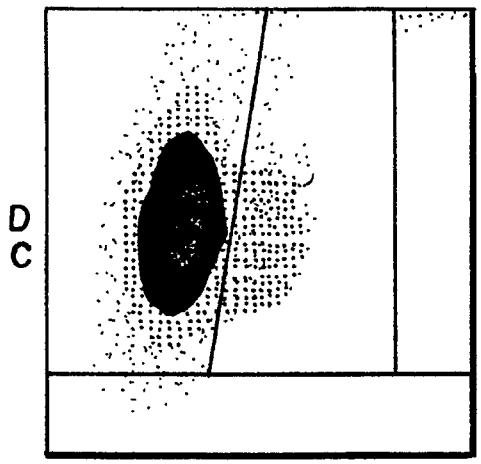
Figure 10C:
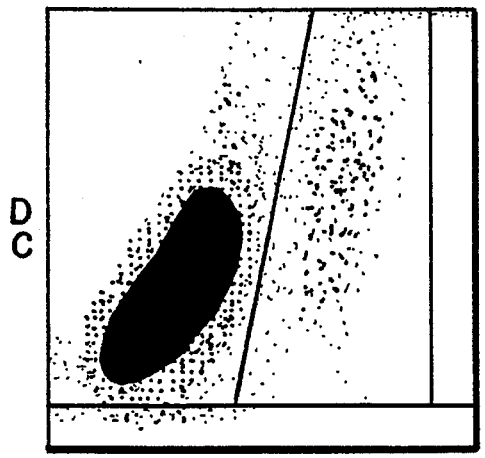
Figure 11A:
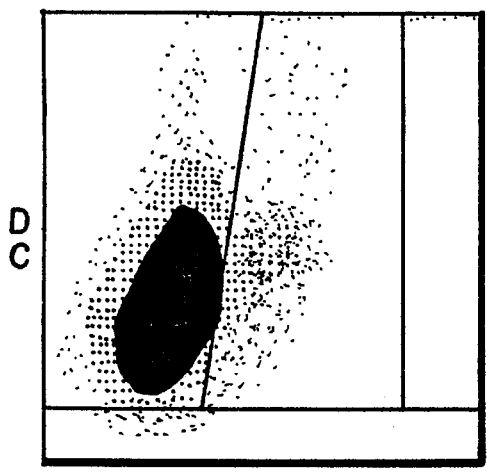
Figure 11B:
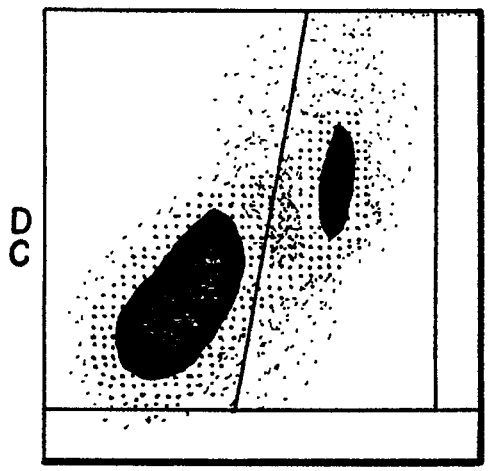
Figure 11C:
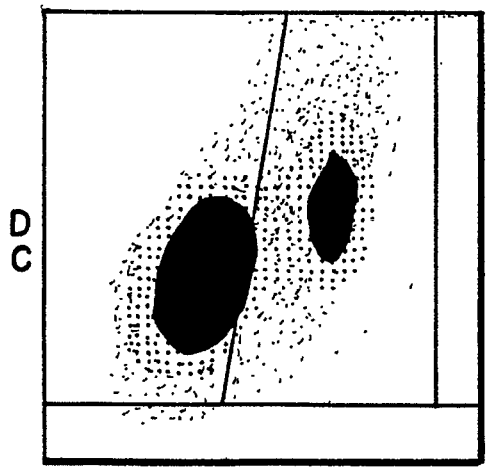

FIGS. 5A–D illustrate the results obtained by analyzing a whole blood sample treated with the staining reagent and with the ghosting reagent and analyzed with the particle analyzer or flow cytometer of FIG. 2. at various angles of light scatter. Each of the four figures display a data matrix of a light scatter measurement on the x axis vs. DC on the y axis with a reticulocyte population 280 to the right of the mature erythrocyte population 282. FIG. 5A displays a data matrix of LOG LMALS vs. DC. FIG. 5B displays a data matrix of LOG UMALS vs. DC. FIG. 5C displays a data matrix of LOG SALS vs. DC. FIG. 5D displays a data matrix of LOG RALS vs. DC. From the data presented in FIGS. 5A–D and the description thereof, it has been demonstrated that reticulocytes, treated with at least a ghosting reagent, can be identified and enumerated by analyzing with light scatter, and that the light scatter can be collected at any of a variety of different angles, without using fluorescence. UMALS is the preferred light scatter angle, and will be used exclusively throughout the remainder of this specification.

In the methods illustrated in FIGS. 3A–C and throughout this specification the step of obtaining RBC can be implemented in two different procedures. Referring to FIG. 2, the first procedure involves performing the absolute erythrocyte count on the same blood sample which is treated and analyzed for reticulocyte classification and enumeration, and performing the count at the same time the blood cells 50 traverse the aperture or sensing zone 12. Any of the simultaneously measured parameters, such as DC, RF, LMALS, UMALS, SALS and RALS, can be utilized to obtain the absolute erythrocyte count, RBC. DC is the preferred parameter for obtaining RBC. The second procedure for obtaining RBC is to use another apparatus, a particle or blood cell counter (for example, the COULTER® STKS sold by the assignee of the present invention), which can be physically attached to the reticulocyte analyzer of, for example, FIG. 2, or which can be part of another instrument. Using either the first or second procedure to obtain RBC, the RBC and RETIC% results are combined to compute RETIC-ABS.

FIGS. 6A–C and FIGS. 7A–G illustrate data classification methods applicable to data generated by any of the methods of FIGS. 3A–C. The methods of FIG. 3C, involving treating a blood sample with Staining Reagent #1 and Ghosting Reagent #1, and analyzing the treated sample with at least UMALS in a particle analyzer, for example such as illustrated in FIG. 2, provide the optimum configuration for practicing this invention, and provide the reticulocyte data illustrated in FIGS. 6A–C.

FIGS. 6A, 6B and 6C illustrate numerous data classification methods where the reticulocytes are classified and enumerated utilizing at least a combination of LLS and DC. With the classification method illustrated by FIG. 6A, a boundary 290 separates a thrombocyte population 292 from populations of erythrocytes 294, 296, 298 and leucocytes 300 utilizing DC. Utilizing LLS, a boundary 302 separates the mature erythrocytes 294 from the reticulocytes 296, 298. A boundary 304 separates the reticulocytes 296, 298 from the leucocytes 300. A boundary 306 separates LSR 296 from HSR 298. Thus, it can be concluded from FIG. 6A, that utilizing a combination of LLS and DC, and treating the blood sample with the staining and the ghosting reagents, a classification can be made of the thrombocytes 292, the leucocytes 300, the mature erythrocytes 294 and the reticulocytes 296, 298, and that the reticulocytes 296, 298 can be subclassified into LSR 296 and HSR 298.

Another method for achieving the just described classification is by analyzing one-dimensional histograms one at a time, applying the "gating" technique defined earlier.

1. Utilizing a DC histogram, FIG. 6C, find the boundary 290 or valley which separates the thrombocyte population 292 from a single peak 308 which contains the erythrocytes and leucocytes.
2. Gating on DC values greater than the boundary 290 of FIG. 6C, which effectively removes the thrombocytes 292 from subsequent analysis, generate LLS histogram, FIG. 6B, and utilizing that histogram perform the following steps:
   a) Find the boundary 302 which separates mature erythrocytes 294 from the reticulocytes 296, 298; count the mature erythrocytes 294 from the origin (leftmost extreme) of the histogram to the boundary 302;
   b) Find the boundary 304 which separates the reticulocytes 296, 298 from the leucocytes 300; count the reticulocytes 296, 298 from the boundary 302 to the boundary 304;
   c) Find the boundary 306 which separates LSR 296 from HSR 298; count LSR 296 from the boundary 302 to the boundary 306; count HSR 298 from the boundary 306 to the boundary 304.
3. Gating on DC values greater than the boundary 290 of FIG. 6C, and gating on LLS values greater than the boundary 302 and LLS value less than the boundary 304 of FIG. 6B, generate a DC histogram (not shown) of reticulocytes only and perform statistical analysis of those reticulocytes to yield DC mean.
4. Compute the following results:
   a) Compute total erythrocytes=mature erythrocytes+reticulocytes;
   b) Compute RETIC%=(reticulocytes/total erythrocytes)*100;
   c) Compute MRV=DC mean*calibration factor;
   d) Compute RMI=HSR/reticulocytes.
5. Obtain RBC as previously described and compute RETIC-ABS=RETIC%*RBC.

Another method for reticulocyte classification and enumeration involves utilizing only LLS.

1. Generate a LLS histogram, such as shown in FIG. 6B, and utilizing that histogram perform the following steps:

a) Find the boundary 302 which separates the mature erythrocytes 294 from the reticulocytes 296, 298; count the mature erythrocytes 294 from the origin (leftmost extreme) of the histogram to the boundary b) Find the boundary 304 which separates the reticulocytes 296, 298 from the leucocytes 300; count the reticulocytes 296, 298 from the boundary 302 to the boundary 304;

c) Find the boundary 306 which separates LSR 296 from HSR 298; count LSR 296 from the boundary 302 to the boundary 306; count HSR 298 from the boundary 306 to the boundary 304.

2. Compute the following results:
    a) Compute RETIC%=(reticulocytes/total erythrocytes)*100;
    b) Compute RMI=HSR/reticulocytes.

3. Obtain RBC as previously described and compute RETIC-ABS=RETIC%*RBC.

A drawback of the just described method is that thrombocytes are not excluded from the analysis and can distort the RETIC% and other results. The preferred method requires a DC or some other equivalent measurement of cell volume, taken with the light scatter measurement for each blood cell, which can be utilized to discriminate and to eliminate thrombocytes from the reticulocyte analysis.

FIGS. 7A–G illustrate numerous data classification methods where reticulocytes are classified and enumerated utilizing at least a combination of LLS and DC, preferably the combination of LLS, DC, RLS and "OP", which is an abbreviation for opacity. Where applicable, the same numerals are utilized as utilized in FIGS. 6A–C.

With the classification method of FIG. 7A, the boundary 290 separates the thrombocytes 292 from the erythrocyte population 294 and 310 and the leucocytes 300 utilizing DC. Utilizing LLS, a slanted boundary 312 separates the mature erythrocytes 294 from the reticulocytes 310. The boundary 304 separates the reticulocytes 310 from the leucocytes 300. Thus, it can be concluded from FIG. 7A, that utilizing a combination of LLS and DC, and treating the blood sample with the staining and ghosting reagents, a classification and enumeration can be made of the thrombocytes 292, the leucocytes 300, the mature erythrocytes 294 and the reticulocytes 310. In addition, the following results can be reported: RETIC%, MRV and, by obtaining RBC, RETIC-ABS.

The classification method illustrated by FIG. 7B is combined with the just described method illustrated by FIG. 7A to expand and refine the results obtained. The data pattern shown in FIG. 7B is equivalent to the pattern of FIG. 7A with the exception that RLS is displayed on the x axis, resulting in a rotation of the data, and that the leucocytes 300 on FIG. 7A are gated-out or excluded from the analysis. In FIG. 7B, the boundary 290 separates the thrombocytes 292 from the erythrocytes 314, 316, 318; a boundary 320 separates the mature erythrocytes 314 from the reticulocytes 316, 318; a boundary 322 separates LSR 316 from HSR 318. The advantage of working with the RLS parameter is that the boundaries 320, 322 can be found that are completely orthogonal to the x and y axes. The boundary 320 of FIG. 7B, when projected onto FIG. 7A shows up as the sloping line 312. Thus, the rotated parameter RLS, utilized in conjunction with LLS and DC, and utilized to analyze a blood sample treated with the staining and the ghosting reagents, provides a preferred method of classifying and enumerating the reticulocytes, yielding the following results: RETIC%, MRV, RMI and, by obtaining RBC, RETIC-ABS.

The classification method illustrated by FIG. 7C is combined with the just described methods illustrated by FIGS. 7A–B to further refine the results obtained. FIG. 7C illustrates a matrix of OP vs. DC. The boundary 290 separates the thrombocytes 292 from all other cell populations being analyzed 324, 326 by DC. A boundary 328 separates the cluster 324 including the erythrocytes and leucocytes from the thrombocyte or platelet clumps 326. The platelet clumps 326 are easily identified and gated-out or removed from further analysis utilizing opacity, as illustrated in FIG. 7C. Referring to FIG. 7A, the platelet clumps, if not identified and gated-out by opacity, may overlap with the mature erythrocytes 294 and the reticulocytes 310, distorting the RETIC% and other results. Platelet clumps occur infrequently, but should not interfere with the analysis of reticulocytes. Thus the OP parameter, utilized in conjunction with DC, LLS and RLS, and utilized to analyze a blood sample treated with the staining and ghosting reagents, provides a preferred method of classifying and enumerating the reticulocytes, yielding the following results: RETIC%, MRV, RMI and, by obtaining RBC, RETIC-ABS.

Another way of achieving the just described classification, illustrated by FIGS. 7A–C, is by analyzing one-dimensional histograms FIGS. 7D–G one at a time, applying the "gating" technique defined earlier.

1. Utilizing a DC histogram, FIG. 7E, find the boundary 290 which separates the thrombocytes 292 from a single peak 330 which contains the erythrocytes, leucocytes and platelet clumps.

2. Gating on DC values greater than the boundary 290 of FIG. 7E, which effectively removes the thrombocytes 292 from the subsequent analysis, generate a OP histogram, FIG. 7G, and utilizing that histogram, find the boundary 328 which separates the erythrocytes and leucocytes 324 from the platelet clumps 326.

3. Gating on DC values greater than the boundary 290 of FIG. 7E, which effectively removes the thrombocytes 292 from the subsequent analysis, and also gating on values less than the boundary 328 of FIG. 7G, which effectively removes the platelet clumps 326 from the subsequent analysis, generate a LLS histogram, FIG. 7D, and utilizing that histogram, find the boundary 304 which separates the erythrocytes 294, 310 from the leucocytes 300.

4. Gating on DC values less than the boundary 290 of FIG. 7E, which effectively removes the thrombocytes 292 from the subsequent analysis, also gating on OP values less than the boundary 328 on FIG. 7G, which effectively removes the platelet clumps 326 from the subsequent analysis, and also gating on LLS values less than the boundary 304 of FIG. 7D, which effectively removes the leucocytes 300 from the subsequent analysis, generate a RLS histogram, FIG. 7F, and utilizing that histogram, perform the following steps:

a) Find the peak of the mature erythrocyte population 314;
    b) Fit a normal probability function curve on the mature erythrocytes peak 314;
    c) Find the boundary 320 which separates the mature erythrocytes 314 from the reticulocytes 316, 318 by computing the channel at which the fitted curve and the remaining data overlap at equal probabilities; count the mature erythrocytes 314 from the origin (leftmost extreme) of the histogram to the boundary 320;
    d) Find the boundary 322 which separates LSR 316 from HSR 318; count LSR 316 from the boundary 320 to the boundary 328; count HSR 318 from the boundary 322 to the maximum (rightmost extreme) of the histogram.

5. Gating on DC values greater than the boundary 292 of FIG. 7E, gating on OP values less than the boundary 328 on FIG. 7G, gating on LLS values less than the boundary 304 of FIG. 7D, and gating on RLS values greater than the boundary 320 of FIG. 7F, generate a DC histogram (not shown) of the reticulocytes only and perform statistical analysis of those reticulocytes to yield DC mean.

6. Compute the following results:
   a) Compute total erythrocytes=mature erythrocytes+ reticulocytes;
   b) Compute RETIC%=(reticulocytes/total erythrocytes)*100;
   c) Compute MRV=DC mean*calibration factor;
   d) Compute RMI=HSR/reticulocytes.

7. Obtain RBC as previously described and compute RETIC-ABS=RETIC%*RBC.

FIGS. 8A–C, 9A–C, 10A–C and 11A–C show examples of human blood specimens prepared with the reticulocyte treatment method of FIG. 3C, analyzed with at least UMALS and DC in an apparatus as illustrated in FIG. 2 and classified by the methods illustrated by FIGS. 7A–G. The plots in each of the FIGS. 8–11 are depicted the same as in FIG. 7A, but without boundary and population numerals. The actual reticulocyte classifications are illustrated for each of FIGS. 6–11.

Figure 12:
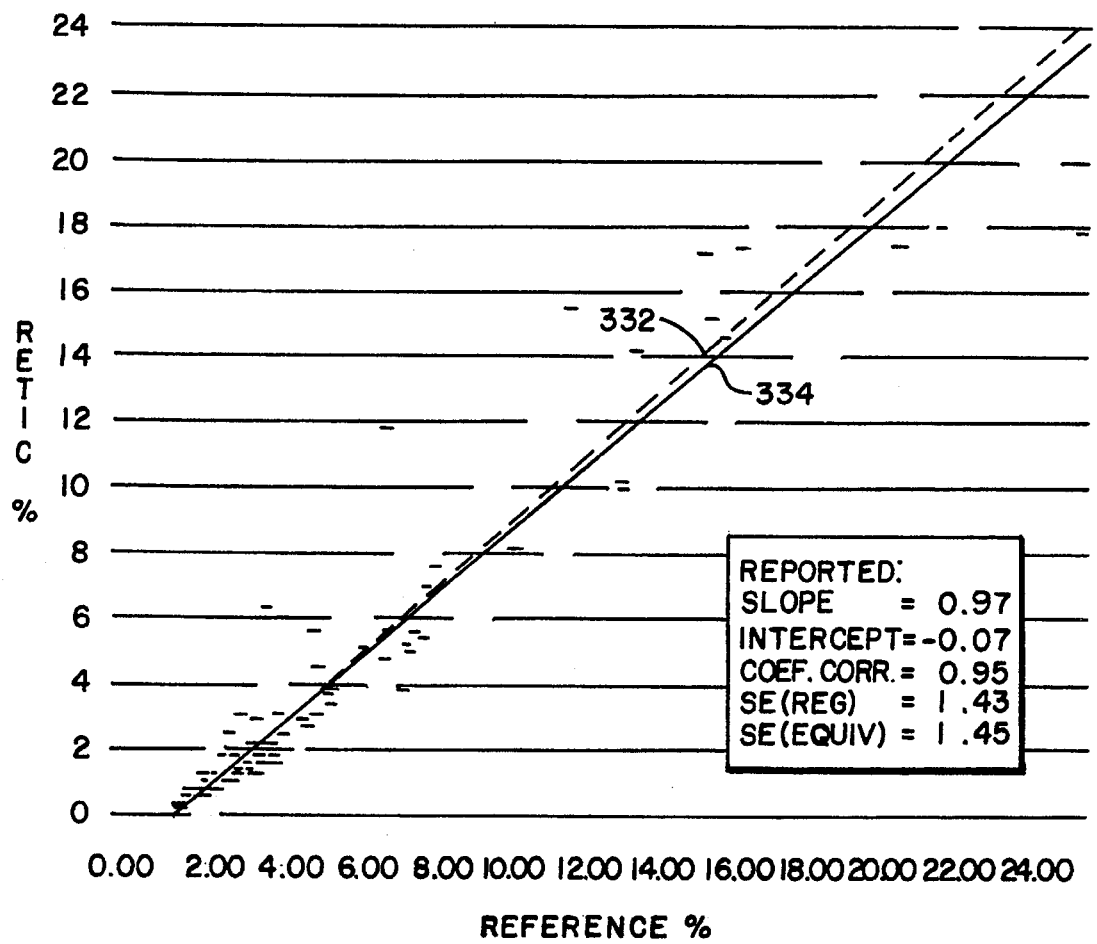
FIG. 12 illustrates a plot of reticulocyte percent obtained with the present invention vs. reticulocyte percent obtained with the reference method.

FIG. 12 shows a correlation study of human blood specimens with the "REFERENCE%" plotted on the x axis and "RETIC%" on the y axis. "REFERENCE%" is the reticulocyte percentage obtained by the reference method outlined in the proposed NCCLS standard, H16-P. The "RETIC%" is the result generated by the preferred methods and apparatus as described earlier. A dotted 45° line 332 represents a perfect data fit or a correlation coefficient of 1.0. The actual data fit is illustrated by a solid line 334. The difference between the two lines represents a correlation coefficient of 0.95.

We claim:

1. A method of determining a percent of reticulocytes to the total number of erythrocytes in at least a portion of a whole blood sample in a cytometric flow cell, comprising:
   a. combining a portion of a whole blood sample, including a plurality of cells, with a RNA precipitating first dye, said first dye being used to delineate reticulocytes for light scatter detection of said reticulocytes;
   b. combining said portion of a whole blood sample including a plurality of cells with a red blood cell ghosting reagent which removes hemoglobin from said red blood cells;
   c. passing an aliquot of said combined whole blood sample, RNA precipitating first dye and ghosting reagent through a cytometric flow cell, including passing said cells substantially one at a time through a sensing zone in said cytometric flow cell and concurrently passing at least a beam of light through said sensing zone to intersect said cells;
   d. detecting light scattered caused by each cell as each cell intersects said beam of light; and
   e. analyzing upper median angle light scatter (UMALS) of said light scattered by each cell to obtain a determination of the percentage of reticulocytes to the total number of erythrocytes in said whole blood sample.

2. The method of claim 1 which further includes a determination of a Reticulocyte Maturity Index of the reticulocytes in the whole blood sample, said Index being a ratio of the count of higher intensity light scatter reticulocytes (HSR) to a total reticulocyte count in said portion of said whole blood sample.

3. The method of claim 2 which further includes electronically sensing each cell as each cell passes through said sensing zone and analyzing said light scatter and said electronic sensing to obtain a determination of a mean reticulocyte volume of the reticulocytes in the whole blood sample.

4. The method of claim 3 wherein the electronically sensing of each cell is by a DC parameter.

5. The method of claim 1 which further includes electronically sensing each cell as each cell passes through said sensing zone and analyzing said light scatter and said electronic sensing to obtain a determination of a mean reticulocyte volume of the reticulocytes in the whole blood sample.

6. The method of claim 1 which further comprises combining said portion of said blood sample with a fluorescent second dye in addition to the RNA precipitating first dye and detecting said fluorescent second dye as each cell passes through the sensing zone of said cytometric flow cell.

7. An apparatus for determining a percent of reticulocytes to the total number of erythrocytes in at least a portion of a whole blood sample in a cytometric flow cell, comprising:
   a. means for combining a portion of a whole blood sample, including a plurality of cells, with a RNA precipitating first dye, said first dye being used to delineate reticulocytes for light scatter detection of said reticulocytes;
   b. means for combining said portion of a whole blood sample, including a plurality of cells, with a red blood cell ghosting reagent which removes hemoglobin from said red blood cells;
   c. means for passing an aliquot of said combined whole blood sample, RNA precipitating first dye and ghosting reagent through a cytometric flow cell, wherein said flow cell includes means for passing said cells substantially one at a time through a sensing zone in said cytometric flow cell and concurrently passing at least a beam of light through said sensing zone to intersect said cells;
   d. means for detecting light scattered caused by each cell as each cell intersects said beam of light; and
   e. means for analyzing upper median angle light scatter(UMALS) of said light scattered by each cell to obtain a determination of the percentage of reticulocytes to the total number of erythrocytes in said whole blood sample.

8. The apparatus defined in claim 7 including means for a determination of a Reticulocyte Maturity Index of the reticulocytes in the whole blood sample, said Index being a ratio of the count of higher intensity light scatter reticulocytes (HSR) to a total reticulocyte count in said portion of said whole blood sample.

9. The apparatus defined in claim 8 which further includes means for electronically sensing each cell as each cell passes through said sensing zone and analyzing said light scatter and said electronic sensing to obtain a determination of a mean reticulocyte volume of the reticulocytes in the whole blood sample.

10. The apparatus defined in claim 9 wherein the electronically sensing of each cell is by a DC parameter.

11. The apparatus defined in claim 7 which further includes means for electronically sensing each cell as each cell passes through said sensing zone and analyzing said light scatter and said electronic sensing to obtain a determination of a mean reticulocyte volume of the reticulocytes in the whole blood saple.

12. The apparatus defined in claim 7 which further includes a means for combining said portion of said blood sample with a fluorescent second dye in addition to the RNA precipitating first dye and means for detecting said fluorescent second dye as each cell passes through the sensing zone of said cytometric flow cell.

13. A method of determining reticulocyte count in at least a portion of a whole blood sample in a cytometric flow cell, comprising:
   a. combining a portion of a whole blood sample, including a plurality of cells, with a RNA precipitating first dye, said first dye being used to delineate reticulocytes for facilitating light scatter detection of said reticulocytes;
   b. combining said portion of a whole blood sample including a plurality of cells with a red blood cell ghosting reagent which removes hemoglobin from said red blood cells;
   c. passing an aliquot of said combined whole blood sample, RNA precipitating first dye and ghosting reagent through a cytometric flow cell, including passing said cells substantially one at a time through a sensing zone in said cytometric flow cell and concurrently passing at least a beam of light through said sensing zone to intersect said cells;
   d. detecting light scattered caused by each cell as each cell intersects said beam of light; and
   e. analyzing upper median angle light scatter (UMALS) of said light scattered by each cell to obtain a determination of the number of reticulocytes in said blood sample.

14. The method of claim 1 which further includes a determination of a Reticulocyte Maturity Index of the reticulocytes in the whole blood sample, said index being a ratio of the count of higher intensity light scatter reticulocytes (HSR) to a total reticulocyte count in said portion of said whole blood sample.

15. The method of claim 14 which further includes electronically sensing each cell as each call passes through said sensing zone and analyzing said light scatter and said electronic sensing to obtain a determination of a mean reticulocyte volume of the reticulocytes in the whole blood sample.

16. The method of claim 15 wherein the electronically sensing of each call is by a DC parameter.

17. The method of claim 13 which further includes electronically sensing each cell as each cell passes through said sensing zone and analyzing said light scatter and said electronic sensing to obtain a determination of a mean reticulocyte volume of the reticulocytes in the whole blood sample.

18. The method of claim 13 which further comprises combining said portion of said blood sample with a fluorescent second dye in addition to the RNA precipitating first dye and detecting said fluorescent second dye as each cell passes through the sensing zone of said cytometric flow cell.

19. An apparatus for determining reticulocyte count in at least a portion of a whole blood sample in a cytometric flow cell, comprising:
   a. means for combining a portion of a whole blood-sample,. including a plurality of cells, with a RNA precipitating first dye, said first dye being used to delineate reticulocytes for light scatter detection of said reticulocytes;
   b. means for combining a portion of a whole blood sample, including a plurality of cells with a red blood cell ghosting reagent which removes hemoglobin from said red blood cells;
   c. means for passing an aliquot of said combined whole blood sample, RNA precipitating first dye and ghosting reagent through a cytometric flow cell, wherein said flow cell includes means for passing said cells substantially one at a time through a sensing zone in said cytometric flow cell and concurrently passing at least a beam of light through said sensing zone to intersect said cells;
   d. means for detecting light scattered caused by each cell as each cell intersects said beam of light; and
   e. means for analyzing upper median angle light scatter (UMALS) of said light scattered by each cell to obtain a determination of the number of reticulocytes in said blood sample.

20. The apparatus defined in claim 19 including means for a determination of a Reticulocyte Maturity Index of the reticulocytes in the whole blood sample, said Index being a ratio of the count of higher intensity light scatter reticulocytes (HSR) to a total reticulocyte count in said portion of said whole blood sample.

21. The apparatus defined in claim 20 which further includes means for electronically sensing each cell as each cell passes through said sensing zone and analyzing said light scatter and said electronic sensing to obtain a determination of a mean reticulocyte volume of the reticulocytes in the whole blood sample.

22. The apparatus defined in claim 21 wherein the electronically sensing of each cell is by a DC parameter.

23. The apparatus defined in claim 19 which further includes means for electronically sensing each cell as each cell passes through said sensing zone and analyzing said light scatter and said electronic sensing to obtain a determination of a mean reticulocyte volume of the reticulocytes in the whole blood sample.

24. The apparatus defined in claim 19 which further includes a means for combining said portion of said blood sample with a fluorescent second dye in addition to the RNA precipitating first dye and means for detecting said fluorescent second dye as each cell has passes through the sensing zone of said cytometric flow cell.

\* \* \* \* \*